United States Patent
Suh et al.

(10) Patent No.: US 6,907,358 B2
(45) Date of Patent: Jun. 14, 2005

(54) EDDY CURRENT INSPECTION METHOD

(75) Inventors: Ui Won Suh, Cincinnati, OH (US); Clifford Sneed, Jr., Cincinnati, OH (US)

(73) Assignee: General Electric Company, Schenectady, NY (US)

( * ) Notice: Subject to any disclaimer, the term of this patent is extended or adjusted under 35 U.S.C. 154(b) by 277 days.

(21) Appl. No.: 10/355,810

(22) Filed: Jan. 30, 2003

(65) Prior Publication Data

US 2004/0153260 A1 Aug. 5, 2004

(51) Int. Cl.$^7$ .............................................. G06F 19/00
(52) U.S. Cl. .................................. 702/38; 382/152
(58) Field of Search .......................... 702/38, 36, 35; 382/152; 73/865.8, 583; 166/66.5, 66; 175/24; 376/249

(56) References Cited

U.S. PATENT DOCUMENTS

| | | | |
|---|---|---|---|
| 5,345,514 A | * | 9/1994 | Mahdavieh et al. ........ 382/152 |
| 5,442,286 A | | 8/1995 | Sutton et al. |
| 5,479,834 A | | 1/1996 | Sanagawa et al. |
| 5,537,334 A | * | 7/1996 | Attaoui et al. ................. 702/35 |
| 2003/0089183 A1 | * | 5/2003 | Jacobsen et al. ........... 73/865.8 |

OTHER PUBLICATIONS

U.S. patent application No. 10/011,190; filed Dec. 7, 2001; Dziech et al.

* cited by examiner

*Primary Examiner*—John Barlow
*Assistant Examiner*—Xiuqin Sun
(74) *Attorney, Agent, or Firm*—V. G. Ramaswamy; Francis L. Conte

(57) ABSTRACT

A specimen is mounted in a multiaxis machine. An eddy current probe is also mounted in the machine for multiaxis movement relative to the specimen. The probe is aligned in situ with a target in the specimen by direct contact therebetween at multiple alignment sites corresponding with a numerical model of the specimen. Eddy current inspection of the target may then be conducted by moving the probe along multiple inspection sites of the target corresponding with the specimen model.

20 Claims, 4 Drawing Sheets

EDDY CURRENT INSPECTION METHOD

BACKGROUND OF THE INVENTION

The present invention relates generally to non-destructive testing, and, more specifically, to eddy current inspection.

Gas turbine engines include rotating shafts and disks which support rotating blades in the fan, compressor, high pressure turbine, and low pressure turbine. Commercial and military turbine engines used for powering aircraft in flight require minimum weight while still ensuring a suitable useful life of the engine components.

The rotating components are subject to substantial centrifugal loads during operation which generate corresponding stress that must be limited for maximizing component life. Various forms of superalloy materials are commonly used in modern aircraft turbine engines for ensuring component integrity over the useful life thereof.

However, defects, flaws, or other anomalies in the material may be introduced during the original manufacture of the engine components, or may occur during the operational life thereof. Accordingly, the engine components are typically inspected during the manufacturing process, and during routine maintenance outages, for uncovering any anomaly therein which might limit the useful life of the components.

A common, non-destructive inspection technique is eddy current (EC) inspection of typically metal components. An EC probe includes a small electrical coil mounted near the tip thereof through which an alternating current is generated, which in turn produces an eddy current in the component. The probe tip is moved along the surface of a component for inspection and is used to measure the interaction between the electromagnetic field and the component. A defect or geometric abnormality in the material which changes the homogeneity thereof will disturb the eddy current. The disturbed eddy current modifies the exciting current in the probe coil, and the modified current is then suitably detected and correlated to particular properties of the material to indicate the corresponding anomaly.

For example, eddy current inspection is commonly used for measuring residual stress, density, and degrees of heat treatment in typically metal components. It is also typically used for detecting physical defects or abnormalities on or near the material surface such as dents, bumps, or minute cracks in the material.

Crack detection is particularly important in turbine engine components since cracks may propagate under stress and substantially reduce the useful life of a component, and may eventually lead to component failure if not suitably accommodated.

The electrical coil in a typical eddy current probe is relatively small, for example, about 0.5 mm in diameter for ensuring high sensitivity to detect very small flaws or defects in the material. Correspondingly, the small coil is very sensitive to the operating environment of the inspection equipment. For example, the probe must remain in contact with the component or specimen being inspected without any gaps therebetween which would cause false readings.

The face of the coil should be oriented substantially normal or perpendicular to the surface of the specimen for maximizing eddy current inspection performance. And, the contact pressure between the probe and the specimen should remain substantially constant as the probe slides along the specimen in order to maintain integrity of the eddy current signal to prevent lift-off of the probe from the specimen which would interrupt that signal.

Although eddy current inspection may be done manually by hand movement of the probe, automated movement of the probe is desired for ensuring accurate inspection and reducing cost for repetitive inspections of multiple features in various components. However, since the target region of a typical specimen has a changing contour subject manufacturing tolerances it is quite difficult to accurately align the probe and automate the inspection process.

For example, even a simple cylindrical hole has a continuously varying surface around the perimeter thereof which correspondingly requires continuous adjustment of the orientation of the eddy current probe. More complex specimen targets include elliptical holes, as well as serpentine features commonly found in gas turbine engines.

For example, each rotor blade in the engine typically includes a mounting dovetail having serpentine dovetail lobes which may be inspected. The dovetails mount in complementary dovetail slots in the perimeter of rotor disks, which slots may require inspection. And, compressor disks may be joined together at curvic couplings including an annulus of scalloped projections for transmitting torque between the disks, which scallops may also be inspected.

In automating eddy current inspection of these typical gas turbine engine components, a conventional multiaxis computer numerically controlled (CNC) machine may be used for mounting the component specimen and the eddy current probe for relative movement. The typical CNC machine includes three translation axes (X,Y,Z) and one or more rotary axis corresponding with the translation axes. In this way, an EC probe may be mounted in the spindle of the machine for automated translation in the three translation axes, with suitable rotation thereof for positioning the probe tip and coil thereat substantially normal to the target surface of the specimen for eddy current inspection thereof.

However, in order to automate the travel of the probe over the changing surface of the target, the probe must be accurately aligned in the machine relative to the specific component specimen mounted therein. The CNC machine has a memory in which the three dimensional (3D) numerical model of the specimen, as represented by its coordinate drawing is stored, with the machine being programmed to follow the stored model in the particular location of the target region thereof being inspected.

Alignment of the probe and component specimen has been a complex and lengthy process in which a specifically configured template is required. For example, the eddy current inspection of an exemplary oil drain hole in a compressor rotor disk has been conducted for many years in this country for production components sold to and used by customers in this and foreign countries. The drain hole has an elliptical profile in an exemplary embodiment, and a specifically configured template is mounted near the drain hole for permitting initial alignment of the probe with a reference aperture in the template. In this way, a stored model of the drain hole using the coordinate system of the machine may be matched to the template for identifying the actual location of the drain hole mounted in the machine.

The conventional alignment process using the template requires a few hours to complete and is repeated multiple times to attach and detach the template until suitable alignment is achieved. The template may then be removed, and the probe automatically driven by the machine to inspect the inner surface of the drain hole around its perimeter at various depths therein using the stored model of the drain hole for numerically guiding the probe.

Accordingly, it is desired to provide an improved method of eddy current inspection of a specimen target which obviates the need for the alignment template.

BRIEF DESCRIPTION OF THE INVENTION

A specimen is mounted in a multiaxis machine. An eddy current probe is also mounted in the machine for multiaxis movement relative to the specimen. The probe is aligned in situ with a target in the specimen by direct contact therebetween at multiple alignment sites corresponding with a numerical model of the specimen. Eddy current inspection of the target may then be conducted by moving the probe along multiple inspection sites of the target corresponding with the specimen model.

BRIEF DESCRIPTION OF THE DRAWINGS

The invention, in accordance with preferred and exemplary embodiments, together with further objects and advantages thereof, is more particularly described in the following detailed description taken in conjunction with the accompanying drawings in which.

DETAILED DESCRIPTION OF THE INVENTION

Figure 1:
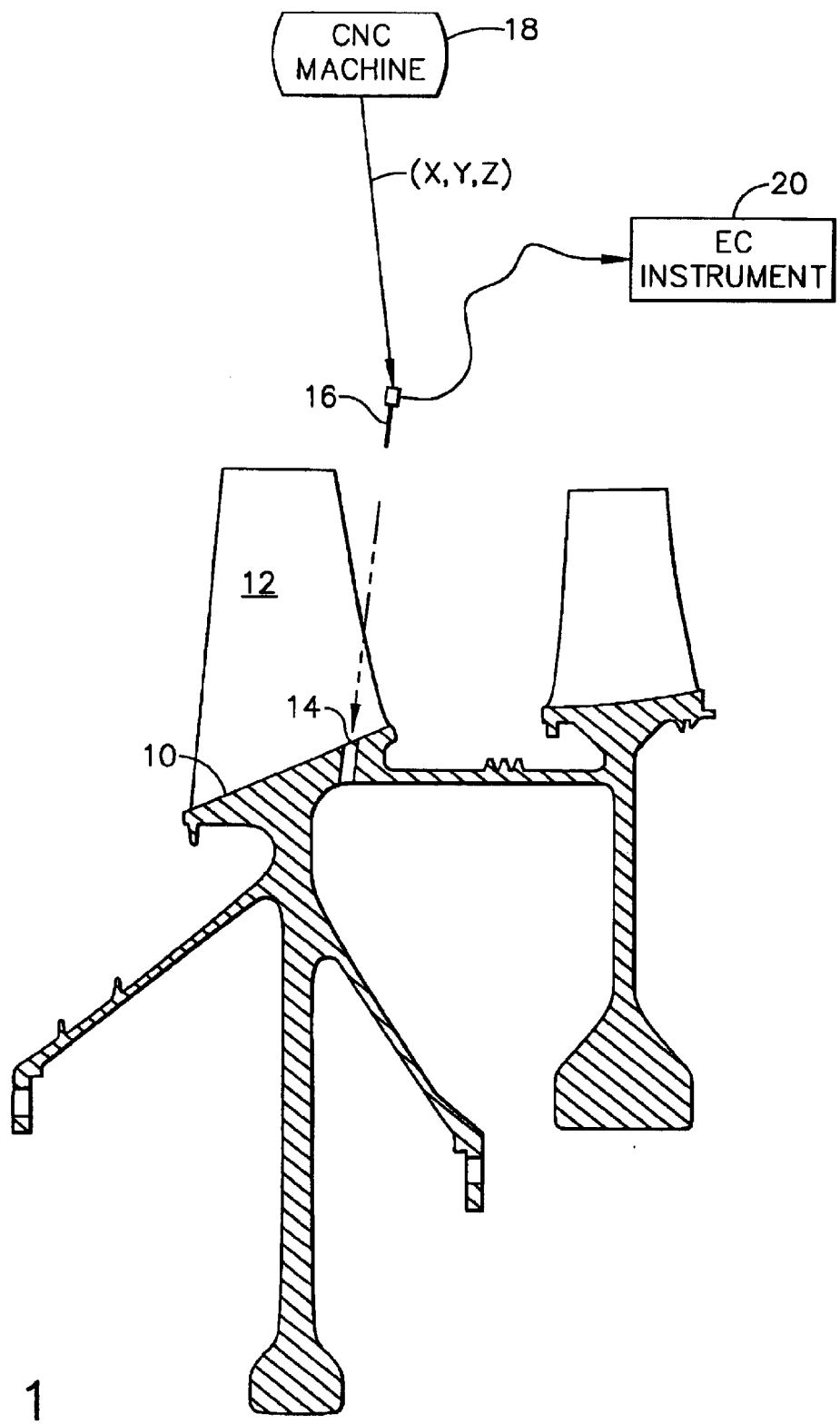
FIG. 1 is a schematic representation of a multiaxis CNC machine configured for performing eddy current inspection of a specimen in the exemplary form of a drain hole target in a compressor rotor disk.

Illustrated in FIG. 1 is a specimen 10 in the exemplary form of a compressor rotor disk for a gas turbine engine. The disk specimen includes an annular rim from which extend radially outwardly a row of compressor rotor blades 12, which are integrally formed therewith in a unitary blisk configuration in this exemplary embodiment. This embodiment also includes a second blisk in a tandem configuration with the first blisk, although any component of the engine or other apparatus may be used as a specimen.

The entire specimen is subject to centrifugal loading during operation in the gas turbine engine and therefore develops centrifugal stress therein. In the exemplary embodiment illustrated in FIG. 1, the specimen includes a local target 14 in the form of a radial oil drain hole extending completely through the rim of the disk specimen between two of the compressor blades.

Eddy current (EC) inspection of the specimen target may be automated by mounting the specimen 10 and an EC probe 16 into a multiaxis computer numerically controlled (CNC) machine 18. The machine may have any conventional configuration for mounting in the bed thereof the disk specimen 10, and mounting in a spindle thereof the probe 16. The probe 16 may have any conventional configuration, and is suitably joined to an eddy current instrument 20 by an electrical lead therebetween for conducting eddy current inspection in a conventional manner.

For example, the CNC machine 18 may be model EC2000, manufactured by General Electric Company, having a place of business at Cincinnati, Ohio. The EC probe 16 may be model QCT-075-6M-DRV manufactured by Quality Control Technology, having a place of business at Cincinnati, Ohio. The EC instrument 20 may be model Uniwest 450Z, manufactured by Uniwest, having a place of business at Pasco, Wash.

The machine is typically configured for three orthogonal translation axis movement of the probe, along three axes X,Y,Z, with rotational motion around one or more of the three translation axes as required for the particular specimen. In this way, the probe may be accurately positioned relative to the specimen and moved therealong with all required degrees of freedom in accordance with software conventionally programmed in the machine.

Figure 2:
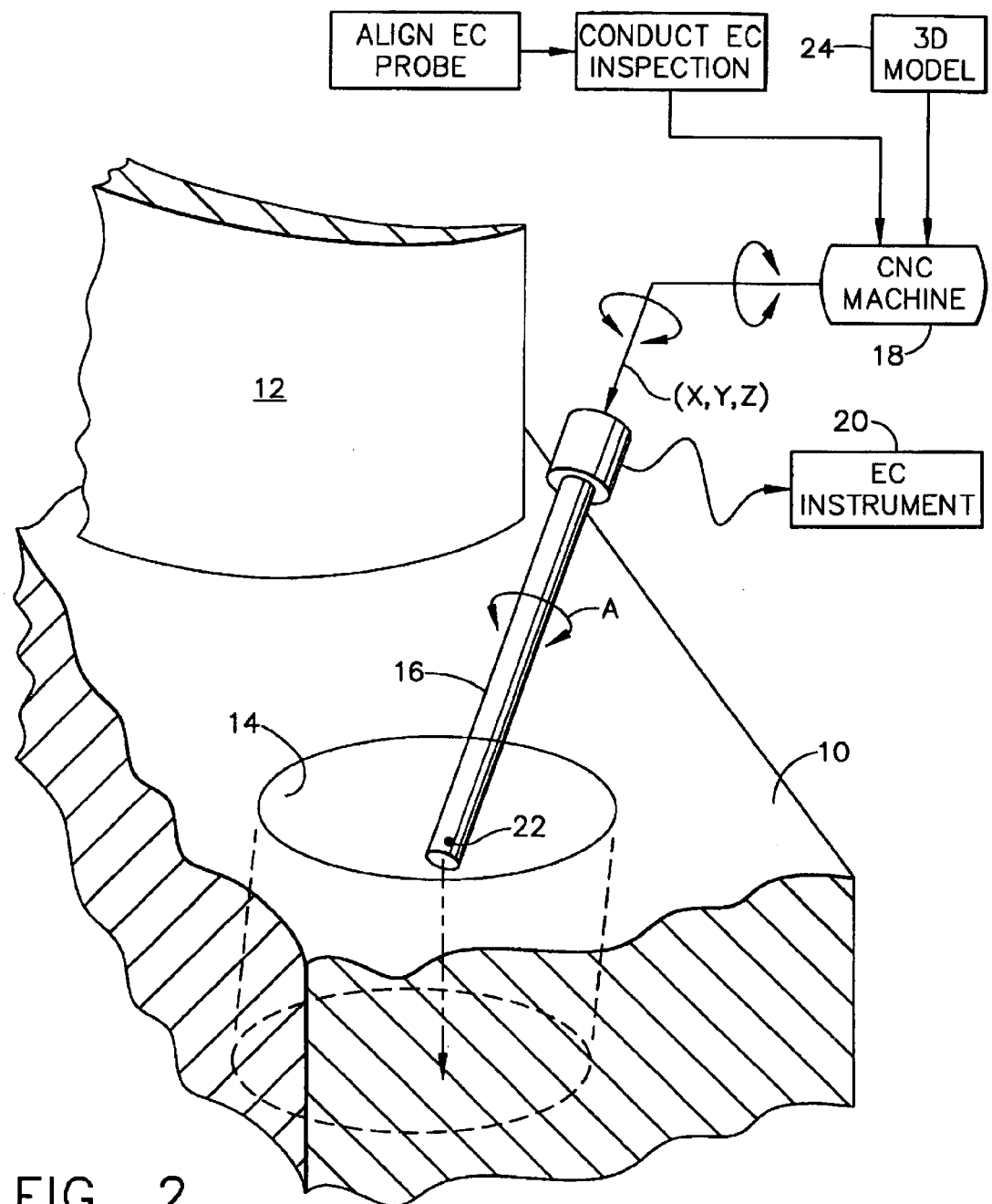
FIG. 2 is a schematic representation of an automated eddy current inspection method of the exemplary drain hole illustrated in FIG. 1.

FIG. 2 illustrates in more detail the exemplary form of the target 14 as being an oil drain hole or aperture extending radially through the rim of the disk specimen 10, and having an elliptical profile cross section. The target therefore defines the elliptical inner surface of the drain hole extending radially through the rim of the specimen.

The probe 16 illustrated in FIG. 2 is mounted in the multiaxis machine 18 with suitable degrees of freedom or motion for reaching the entire inner surface of the drain hole defining the target 14 for which eddy current inspection is desired. The three orthogonal translation axes of movement are X,Y,Z, and the probe may also be rotated with up to three additional rotary degrees of freedom, including rotation A about the longitudinal or rotary centerline axis of the elongate probe 16 itself for effecting intermittent indexing thereof.

The exemplary probe 16 illustrated in FIG. 2 includes an elongate or cylindrical shaft having an electrical eddy current coil 22 located at the cylindrical tip thereof. The coil is suitably small, for example about 0.5 mm in diameter, for providing suitable sensitivity to detect very small anomalies or flaws in the specimen in the target region being inspected. For example, the target may include a small, hairline crack therein, with the coil being sufficiently small and sensitive for detecting and differentiating that crack from the adjacent homogenous material of the specimen.

The small coil 22 is disposed in a locally small circumferential portion along the perimeter of the probe tip, and is thusly available for positioning inside the target within the reach of the elongate shaft of the probe.

As indicated above in the Background section, conventional eddy current inspection requires direct and continuous contact between the probe and the target material, with the probe coil being disposed substantially normal or perpendicular to the target surface. Since the exemplary target 14 illustrated in FIG. 2 is an annular aperture, the probe requires continual repositioning for placing the local coil 22 adjacent the surface of the target as the probe travels around the perimeter thereof.

The CNC machine, like any general purpose computer, must be suitably programmed for its intended function, which for eddy current inspection requires programming of the desired path of the probe 16 along the target 14, as well as suitable alignment of the probe and the specimen when initially mounted in the machine. As indicated above, the previous process for aligning the probe and the specimen in the machine required the use of a specifically configured template associated with the intended target, such as the oil drain hole 14, and required repeated attachment and detachment of the template from the specimen to precisely reference the target to the numerical programming of the machine.

Such previously used aligning templates are no longer required for the improved method disclosed hereinbelow. Instead, the EC probe 16 itself is used in the machine 18 for in situ aligning the probe 16 directly with the actual target 14, not a template joined thereto, by direct contact therebetween at multiple alignment sites corresponding with a numerical model 24 of the specimen, including the desired target 14.

As shown schematically in FIG. 2, the specimen 10, like any manufactured component, may be defined by corresponding drawing specifications including the various three dimensional (3D) coordinates thereof. Various points on the surfaces of the specimen, including points defining the oil drain hole target 14, may be defined using the three coordinates X,Y,Z for each point. The numerical or graphical 3D model 24 of the specimen including the target 14 may be suitably stored in memory in the machine 18.

However, the 3D model 24 is merely mathematical or virtual and must be suitably matched or overlaid with the actual physical location of the specimen 10 as fixedly mounted in the machine 18. This requires suitable alignment, which was previously effected using the template described above.

As indicated above, the probe 16 itself is used without templates in a new procedure for firstly referencing or aligning the probe in situ with the target to match the location of the target with the numerical model 24 of the specimen stored in the machine. In this way, a one-to-one correspondence between the actual location of the specimen in the machine and the virtual model 24 of the specimen may be programmed into the machine to accurately control movement of the probe along the target 14 without excessive or insufficient contact pressure therewith which could damage the probe itself or degrade the eddy current inspection signal.

After suitable alignment of the probe and specimen in the machine, the machine is programmed for automated movement of the probe for conducting eddy current inspection of the target 14 by moving the probe along multiple inspection sites of the target corresponding with the specimen model 24 stored in the machine.

Figure 3:
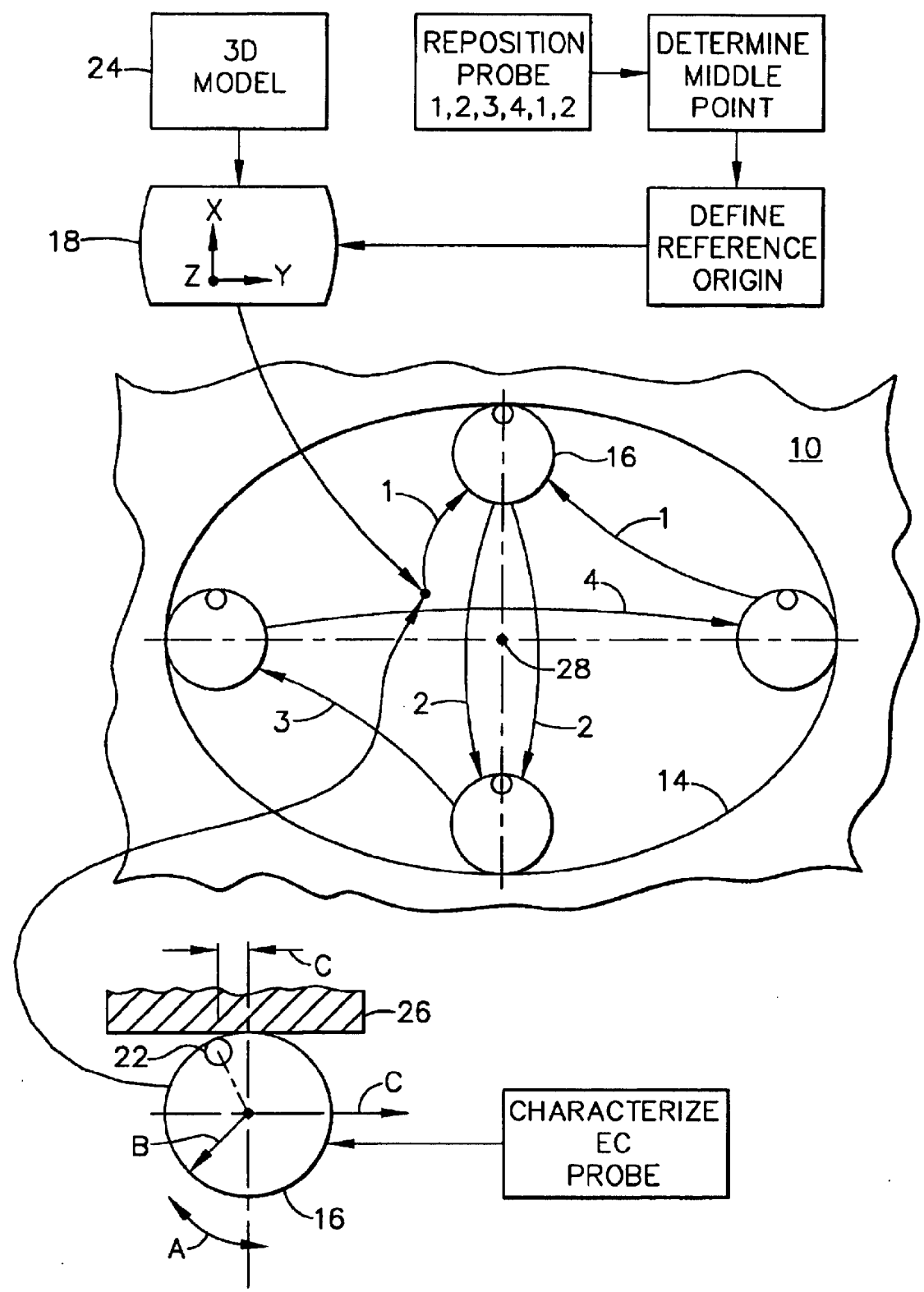
FIG. 3 is a schematic representation of a procedure for initially aligning the probe to the target for determining a reference origin for the numerical model of the target.

An exemplary procedure for aligning the probe 16 with the target 14 is illustrated schematically in FIG. 3. The CNC machine 18 is initially operated manually using conventional controls thereof, such as the typical joystick, for preferentially repositioning the probe at multiple alignment sites along the target and obtaining or measuring corresponding coordinates therefor. FIG. 3 illustrates a top view of the aperture target 14 illustrated in FIG. 2 in an exemplary X-Y spatial plane relative to the control system of the machine itself.

Upon initial mounting of the specimen in the machine, the machine is blind to the accurate location of that specimen. Accordingly, an initial step in the alignment procedure is to locate or define a reference origin or a zero position in the coordinate space of the machine. By defining the reference origin in the X,Y,Z coordinate system of the machine, a direct correspondence with the numerical model 24 stored in the machine may be obtained so that programming movement of the probe based on the numerical model can match in reality the actual location in space of the physical specimen fixedly mounted in the machine.

FIG. 3 additionally illustrates a tip section of the probe 16 including the electrical coil 22 disposed at the perimeter thereof at a radius B from the centerline or rotary axis of the probe tip. The machine 18 is configured or programmed to position the probe to contact the target 14 near the coil 22 for conducting eddy current inspection of the target.

As indicated above, eddy current inspection is conventional and requires the accurate positioning of the probe coil substantially normal to the target surface while maintaining sufficient contact pressure between the probe and the target. However, the machine must be suitably aligned and programmed to the specific geometry of the intended specimen and target for achieving the desired orientation of the probe coil against the target surface.

Illustrated initially at the bottom of FIG. 3 is a radial cross section of the exemplary probe at its operative tip having the coil 22 located at the circumference thereof within the outer radius B relative to the longitudinal rotary axis of the probe. The probe is mounted in the spindle of the machine for controlled rotary indexing or motion A to position the coil in close proximity to the intended specimen.

In order to maximize performance of the probe during eddy current inspection, the probe is first characterized to determine the corresponding linear offset C of the coil 22 from the adjacent tangent of the tip at which contact occurs. For example, FIG. 3 also illustrates a reference block 26 which may be used to characterize the probe, with the probe initially contacting the block at the tangency point. The probe may be indexed in the rotary direction A to position the coil 22 either directly at the tangency point of contact or laterally offset therefrom. The rotary position of the coil may be adjusted during the characterizing procedure to determine its preferred rotary position relative to the reference block for maximizing eddy current performance between the probe and the intended specimen.

In the exemplary embodiment illustrated in FIG. 3, the coil 22 is located at about the eleven o'clock position of the illustrated section of the probe, with the twelve o'clock position of the probe being the contact point with the reference block 26. This exemplary characterized position of the coil relative to the specimen provides maximum sensitivity or performance for conducting eddy current inspection, and results in the corresponding linear offset C along the Y axis, for example. This linear offset C typically has a relatively small magnitude, for example about five mils (0.125 mm).

Accordingly, the entire probe may be translated by the offset C relative to the specimen to align the maximum sensitivity of the coil to the specific location of the target being inspected. Since the probe 16 has a specific geometry and is intended to be moved along the specific geometry of the target 14, the reference origin in the X,Y,Z coordinate system may be further defined to include both the probe radius B and the desired coil offset C as predetermined by the characterization procedure.

The exemplary target 14 illustrated in FIG. 3 is an elliptical aperture in which the correspondingly smaller probe must be accurately moved without over-traveling the boundary defined by that elliptical target. In order to define the reference origin in the machine, the machine is manually operated to move the probe mounted therein inside the target. The probe is repositioned to contact the target aperture at opposite alignment sites 1,2 along the first axis X, and again at opposite alignment sites 3,4 along the different or orthogonal second axis Y to determine a middle point 28 of the target aperture in the XY plane at any suitable location along the Z axis representing the depth into the target aperture.

For example, the machine operator may visually observe the travel of the probe into the target aperture and operate the machine to move that probe to the first alignment site represented in FIG. 3 at the end of the arrow 1 located at the top, middle of the aperture at the twelve o'clock position. The XYZ coordinates of the probe at the first site may then be recorded in the machine.

The probe is then moved to touch the opposite bottom, middle point of the target aperture at the second site 2 along the X axis at the six o'clock position, and the corresponding XYZ coordinates recorded in the machine. From the coordinates for the top and bottom sites along the X axis, the middle position or coordinates therebetween may be calculated in the machine. This calculation represents the vertical middle point in the target aperture along the X axis, but this point may or may not be the middle point horizontally along the second axis Y.

Accordingly, from the vertical middle point, the probe is again moved to the third site 3 at the left middle end of the aperture along the Y axis at the nine o'clock position, and the XYZ coordinates thereof recorded, and then moved again to contact the right middle side of the aperture at the fourth contact site 4 at the three o'clock position, and again the XYZ coordinates at this site are recorded.

The horizontal middle point along the Y axis of the target aperture may then be suitably calculated in the machine. The so-calculated vertical middle point and horizontal middle point of the target aperture 14 may or may not be coincident at the desired middle point 28, but should be relatively close together.

Accordingly, the probe 16 is preferably further repositioned to contact a second time the target aperture at the opposite first and second alignment sites 1,2 which correspond with the original contact sites at the twelve and six o'clock positions to finally confirm or determine the middle point 28 of the target aperture along both X and Y axes. The associated XYZ coordinates at the top and bottom target sites 1,2 may then be used to re-calculate the vertical middle point along the X axis, which vertical middle point should closely match and be substantially coincident with the horizontal middle point along the Y axis. In this way, the middle or center point 28 along both XY axes for the target aperture 14 may be accurately determined and stored within the corresponding memory of the numerically controlled machine.

The reference origin used by the machine for controlling motion of the probe within the target aperture 14 may be located anywhere in space since it provides an indication to the machine of the relative position between the probe itself and the target aperture 14 of the specimen fixedly mounted in the machine. For example, the reference origin may be defined as the middle point 28. However, in the preferred embodiment the reference origin may be defined at any one of the four opposite alignment sites 1,2,3,4 at the ends of the travel arrows and, for example may be the top middle point of the aperture represented by the first alignment site 1 at the twelve o'clock position.

As illustrated schematically in FIG. 3 the movement of the probe between the sites 1-2-3-4-1-2 is visually observed by the operator to just contact the target aperture at those sites, without excessive movement of the probe to avoid damage thereto. Since the outer surface of the probe actually contacts the target aperture during this alignment procedure, the reference origin being defined in the machine preferably includes the probe radius B along the X axis, representing the distance from the rotary axis of the probe to its outer surface at the location of the coil 22.

However, rotary indexing of the probe and the characterized location or offset of the coil 22 are not required in this portion of the alignment procedure since only a reference origin within the target space is being defined in the machine.

Nevertheless, it is desired to use the characterized offset C of the probe in the subsequent eddy current inspection procedures for maximizing sensitivity and performance thereof. Accordingly, the specific lateral offset C determined for the specific form of the probe 16 as determined in the characterizing procedure described above is preferably introduced in the definition of the reference origin along the corresponding coordinate axis therefor. For example, for the exemplary top site 1 illustrated in FIG. 3, the coil offset C may be introduced in the reference origin along the Y axis; along with the probe radius B being introduced in the reference origin along the X axis.

In FIG. 3, the procedure for initially aligning the probe relative to the few alignment sites within the target aperture 14 is presented. In order to align the probe with the entirety of the target aperture 14, the numerical specimen model 24 stored in the machine memory is next fitted or matched to overlay the actual target fixedly mounted in the machine using the reference origin previously defined above. This is illustrated schematically in FIG. 4.

The specimen model 24 is a suitable locus of XY coordinates in each Z plane for a suitable number of points sufficient to define in 3D space the associated target 14 for eddy current inspection. The actual target 14 is typically originally manufactured from a numerical model thereof represented in standard engineering drawings or computer numerical models, such as the specimen model 24 for the exemplary elliptical target aperture 14 illustrated in FIG. 4. However, the specimen model 24 initially stored in the machine is virtual, and must be correlated or aligned with the actual location in space of the corresponding physical target aperture 14 when fixedly mounted in the machine.

Since the reference origin has been accurately determined in the machine using the actual EC probe 16 itself, the next step is to match or overlay the stored specimen model 24 with the actual target aperture relative to the defined reference origin.

By matching in the machine the specimen model 24 to the intended target 14 using the defined reference origin, the probe 16 may be accurately aligned with the intended target, and then the eddy current inspection of the target may be conducted in the conventional manner. The CNC machine 18 may then be suitably programmed for sliding the probe along the target surface within the multiple axis capability movement of the machine for conducting automated eddy current inspection of the target aperture 14 as effected by the translation and rotary motions available in the machine.

Figure 4:
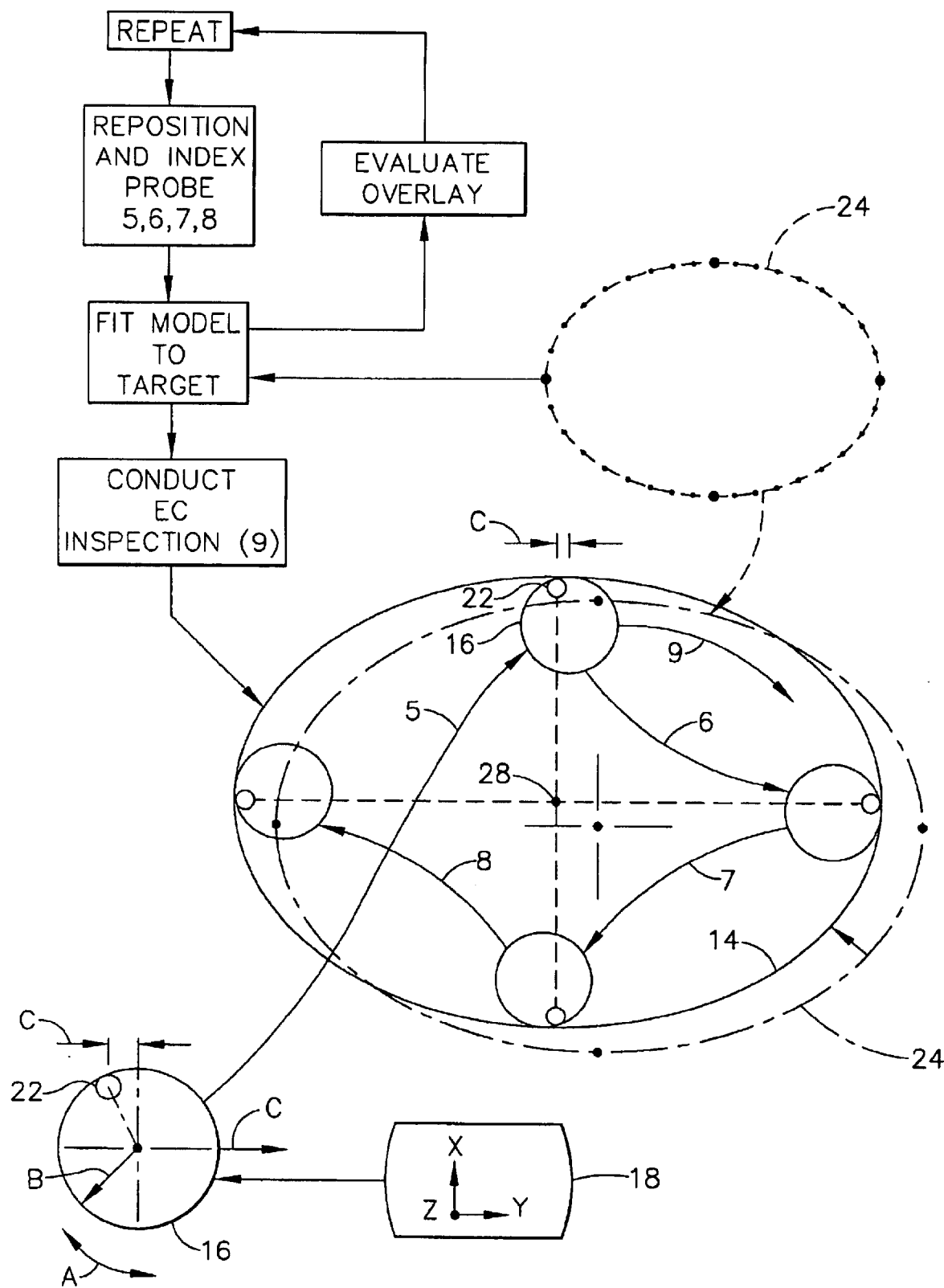
FIG. 4 is a schematic representation of the alignment procedure for matching the specimen model to the actual specimen target for accurately locating the probe to correspond with the numerical model.

In the preferred embodiment illustrated in FIG. 4, the specimen model 24 is matched to the actual target 14 by initially selecting several distributed points from the stored model 24, such as the four corner points at the 3,6,9, and 12 o'clock positions, and overlaying them to their four corresponding points in the physical target. The probe 16 is carefully driven in the machine by the operator to reposition and contact the target at opposite alignment sites 5,7 along the first axis X, and at opposite alignment sites 6,8 along the different second axis Y, all relative to their corresponding points in the model 24. At these four contact sites, corresponding displacements of the probe from their corresponding model points are recorded in the machine.

A first average value of the recorded displacements for the two opposite alignment sites 5,7 along the first axis X is then calculated in the machine. Similarly, a second average value of the recorded displacements for the two opposite alignment sites 6,8 along the second axis Y is then calculated. And, the first and second average values are then compared with a predetermined tolerance to confirm alignment of the probe with the target.

The four distributed alignment sites 5,6,7,8 illustrated at the ends of the travel arrows in FIG. 4 are physical points of the actual target and are being used to overlay the four corresponding points of the specimen model 24. This principle is illustrated schematically in FIG. 4 by the initially remote specimen model 24 which is being aligned in space accurately atop the actual target aperture 14 based on the predetermined reference origin.

It is readily noted that the elliptical specimen model can overlay correctly the elliptical target 14 in only a single orientation, including both relative translation and relative rotation. By matching the stored specimen model 24 to its corresponding actual target aperture 14, the numerically controlled machine 18 may then be used to accurately move the probe along the surface of the target aperture automatically.

A preferred sequence in completing the alignment overlay is shown in FIG. 4. The EC probe 16 is initially moved to the top middle site 5 using the specimen model 24 as the guide, with the coil 22 facing upwardly toward the inner surface of the target. The probe is then slowly moved to actually just touch the target. The displacement along the vertical axis X of the probe from the corresponding model point to the actual position contacting the target is then recorded in the machine.

The probe is then rotated or indexed in the A rotary direction to reposition the coil 22 to the right as illustrated in FIG. 4, with the probe then being repositioned to the right side site 6 again using the specimen model as the guide. Again, the probe is slowly moved to just touch the surface of the target at this sixth site. The corresponding displacement of the probe from the corresponding model point to its position contacting the right side of the target along the horizontal Y axis is then recorded.

The probe 16 is then indexed to position the coil facing downwardly towards the bottom of the aperture, and then the probe is repositioned to the seventh alignment site 7 at the bottom of the aperture again using the specimen model as the guide. The probe is then moved slowly to just contact the surface of the target at this seventh site. Again, the displacement of the probe along the vertical axis X from the corresponding model point to its position contacting the bottom of the aperture at the bottom alignment site 7 is then recorded in the machine.

Lastly, the probe is again indexed to reposition the coil 22 facing to the left, and the probe is then repositioned to the left position of the aperture illustrated in FIG. 4 at the eighth alignment site 8 using the specimen model as the guide. The probe is slowly moved to just touch the target surface at this site. And, the displacement of the probe along the horizontal axis Y from the corresponding model point to its left position contacting the target surface at alignment site 8 is then recorded.

The machine may then be used to calculate the first average value of the recorded displacement for the top and bottom alignment sites 5,7 along the first axis X. The second average value may be calculated in the machine for the displacements for the opposite right and left alignment sites 6,8 along the second axis Y. And then, the so-calculated first and second average values may each be compared with a predetermined tolerance to confirm alignment of the probe 16 with the target 14.

If the four exemplary alignment points chosen from the specimen model 24 accurately overlay the corresponding four physical points on the actual target 14, then the first calculated average value along the X axis will be within the predetermined tolerance, and close to zero, and the second calculated average value along the Y axis will also be within the predetermined tolerance, and close to zero, and the alignment process is complete. It can then be assumed that all points from the specimen model 24 accurately overlay all points of the actual target 14.

However, if the first and second average values are not within the predetermined tolerance, for example, up to about 2 mils (0.05 mm), matching or overlaying between the specimen model and the actual target lacks sufficient accuracy. Accordingly, the reference origin may then be suitably adjusted by both the first and second average values along the corresponding X and Y axes.

For example, the reference origin previously defined may be adjusted or offset along the X axis by the distance represented by the first average value, and along the Y axis by the distance represented by the second average value. More specifically, for the top middle position of the reference origin at site 1 illustrated in FIG. 3 for example, the new reference origin will include the difference of the probe offset C and the horizontal second average value along the Y axis. And, the new reference origin will also include the difference of the probe radius B and the first average value of the displacements along the X axis.

After redefining the reference origin, the procedure illustrated in FIG. 4 may then be repeated to index the coil and reposition the probe at the four corner sites 5,6,7,8, and again recording the displacement between those sites and the corresponding points of the specimen model 24 along the X and Y axes. The first and second averages are then recomputed and should now be better balanced and closer to zero. With the first and second average values being less than the predetermined tolerance, the alignment is finally complete. The so-defined reference origin may then be accurately used as the reference origin for the numerical specimen model 24 stored in the machine to accurately correspond with the mounted location of the specimen and target.

The eddy current inspection of the entire target 14 may then be conducted automatically by the machine using the stored specimen model 24. Suitable instructions are programmed into the machine for moving the probe 16 along the annular movement path 9 illustrated in FIG. 4 to cover the full perimeter of the elliptical target aperture 14 as the corresponding eddy current signals are measured by the eddy current instrument 20 illustrated in FIG. 2. In the preferred embodiment, the CNC machine 18 illustrated schematically in FIG. 4 is suitably programmed to position the moving probe 16 in continuous, sliding contact with the specimen target 14 while maintaining a substantially normal angle of the coil 22 toward the surface thereof, and maintaining a substantially constant contact pressure thereagainst.

The probe 16 can therefore be programmed to continually index or rotate the coil 22 to face the inner surface of the specimen target while maintaining the desired lateral offset C for maximizing eddy current inspection sensitivity and performance. Since the specifically defined reference origin accurately correlates the stored specimen model 24 with the corresponding actual configuration of the specimen target 14 mounted in the machine, automated movement of the probe by the machine can accurately cover the entire surface of the target as represented by the specimen model 24.

The exemplary Z axis illustrated in FIG. 4 extends along the longitudinal or centerline axis of the target aperture 14, and eddy current inspection may be effected at multiple XY planes of the aperture in turn along the Z axis as suitably programmed.

The above described procedure utilizes the actual EC probe 16 itself mounted to the spindle of the machine for initially aligning the probe with the intended specimen target 14 fixedly supported in the machine. The probe itself is preferentially used to define a suitable reference origin for the intended target 14 corresponding with the numerical model 24 stored in the memory of the machine. The reference origin includes a component for the desired lateral offset C of the probe coil 22 as initially determined by characterization thereof, and also includes a component for the actual radius B of the probe at the sensing coil 22.

In this way, an accurate reference origin may be correlated with the specimen model 24 stored in the machine to permit the probe to slide along the entire inner surface of the target aperture 14 as required for automatically conducting the eddy current inspection thereof. And, undesirable lift-off of the probe from the target surface, or excessive pressure between the probe and the target surface, may be eliminated for ensuring effective and reliable eddy current inspection automatically.

By eliminating the previous need for using a specifically configured template for suitably aligning the machine-mounted probe with the machine-mounted specimen target, the costs associated therewith are eliminated, and the initial setup or alignment procedure can be substantially reduced in complexity and time, and associated cost.

The procedure described above may be suitably modified for different forms of specimens and the specific target contained therein which require eddy current inspection. Since automated eddy current inspection requires sliding of the EC probe along the target surface, the procedure above may be practiced for various forms of target surfaces by selecting distributed alignment sites therealong corresponding with associated points in the numerical specimen model of the target stored in the machine. A suitable reference origin may be similarly defined for each form of specimen target which can accurately match the stored specimen model to the actual physical shape of the target as mounted in the machine.

In this way, the EC probe may be suitably programmed to properly orient the characterized probe coil substantially normal to the target surface irrespective of the varying contour of that surface. The probe may be driven by the machine to slide along the target surface while maintaining substantially constant contact pressure therewith and preventing undesirable lift-off of the probe coil therefrom.

While there have been described herein what are considered to be preferred and exemplary embodiments of the present invention, other modifications of the invention shall be apparent to those skilled in the art from the teachings herein, and it is, therefore, desired to be secured in the appended claims all such modifications as fall within the true spirit and scope of the invention.

Accordingly, what is desired to be secured by Letters Patent of the United States is the invention as defined and differentiated in the following claims in which we claim:

1. A method for inspecting a specimen comprising:
   mounting said specimen in a multiaxis machine;
   mounting an eddy current probe in said machine for multiaxis movement relative to said specimen;
   repositioning said probe at multiple alignment sites along said target and obtaining corresponding coordinates therefor;
   defining a reference origin for said target from said coordinates to correspond with a numerical model of said specimen; and
   conducting eddy current inspection of said target by moving said probe along multiple inspection sites of said target corresponding with said specimen model relative to said reference origin.

2. A method according to claim 1 wherein:
   said probe includes a tip having an electrical coil disposed locally along a perimeter thereof at a radius from a rotary axis of said tip; and
   said machine is configured to position said probe to contact said target near said coil for eddy current inspection of said target.

3. A method according to claim 2 further comprising:
   matching said specimen model to said target in said machine using said reference origin for aligning said probe coil with said target; and
   then conducting said eddy current inspection of said target by sliding said probe along said target with multiaxis movement effected by said machine.

4. A method according to claim 3 further comprising:
   characterizing said probe to determine offset of said coil from an adjacent tangent of said tip to maximize performance of said eddy current inspection; and
   defining said reference origin to include said probe radius and coil offset.

5. A method according to claim 4 wherein:
   said target comprises an aperture in said specimen; and
   said probe is repositioned to contact said target aperture at opposite alignment sites along a first axis, and again at opposite alignment sites along a different second axis to determine a middle point of said target aperture for determining said reference origin.

6. A method according to claim 5 wherein matching said specimen model to said target comprises:
   repositioning said probe to contact said target at opposite alignment sites along a first axis, and at opposite alignment sites along a different second axis relative to corresponding points in said specimen model, with said coil being rotated to face said target at each of said opposite alignment sites;
   recording corresponding displacements between said opposite alignment sites and said corresponding model points;
   calculating a first average value of said displacements for said opposite alignment sites along said first axis;
   calculating a second average value of said displacements for said opposite alignment sites along said second axis; and
   comparing each of said first and second average values with a predetermined tolerance to confirm alignment of said probe with said target.

7. A method according to claim 6 wherein said probe is repositioned to contact a second time said target aperture at said opposite alignment sites along said first axis to determine said middle point.

8. A method according to claim 7 wherein said reference origin is defined at one of said opposite alignment sites along said first and second axes.

9. A method according to claim 7 further comprising:
   adjusting said reference origin by both said first and second average values; and
   conducting said eddy current inspection of said target by said machine following said adjustment.

10. A method according to claim 7 further comprising conducting said eddy current inspection of said specimen by sliding said probe in continuous contact with said target along said multiple inspection sites while moving said coil substantially normal to the surface of said target with a substantially constant pressure thereagainst.

11. A method for inspecting a specimen comprising:

mounting said specimen in a multiaxis machine;

mounting an eddy current probe in said machine for multiaxis movement relative to said specimen;

aligning said probe in situ with a target in said specimen by direct contact therebetween at multiple alignment sites corresponding with a numerical model of said specimen; and conducting eddy current inspection of said target by moving said probe along multiple inspection sites of said target corresponding with said specimen model.

12. A method according to claim 11 wherein aligning said probe with said target comprises:

repositioning said probe at multiple alignment sites along said target and obtaining corresponding coordinates therefor; and defining a reference origin for said target from said coordinates to correspond with said model.

13. A method according to claim 12 wherein:

said probe includes a tip having an electrical coil disposed locally along a perimeter thereof at a radius from a rotary axis of said tip; and said machine is configured to position said probe to contact said target near said coil for eddy current inspection of said target.

14. A method according to claim 13 further comprising:

characterizing said probe to determine offset of said coil from an adjacent tangent of said tip to maximize performance of said eddy current inspection; and defining said reference origin to include said probe radius and coil offset.

15. A method according to claim 14 wherein:

said target comprises an aperture in said specimen; and said probe is repositioned to contact said target aperture at opposite alignment sites along a first axis, and again at opposite alignment sites along a different second axis to determine a middle point of said target aperture for determining said reference origin.

16. A method according to claim 15 wherein said probe is repositioned to contact a second time said target aperture at said opposite alignment sites along said first axis to determine said middle point.

17. A method according to claim 16 wherein said reference origin is defined at one of said opposite alignment sites along said first and second axes.

18. A method according to claim 14 further comprising:

matching said specimen model to said target in said machine using said reference origin for aligning said probe with said target; and then conducting said eddy current inspection of said target by sliding said probe along said target with multiaxis movement effected by said machine.

19. A method according to claim 18 wherein matching said specimen model to said target comprises:

repositioning said probe to contact said target at opposite alignment sites along a first axis, and at opposite alignment sites along a different second axis relative to corresponding points in said specimen model, with said coil being rotated to face said target at each of said opposite alignment sites;

recording corresponding displacements between said opposite alignment sites and said corresponding model points;

calculating a first average value of said displacements for said opposite alignment sites along said first axis;

calculating a second average value of said displacements for said opposite alignment sites along said second axis; and comparing each of said first and second average values with a predetermined tolerance to confirm alignment of said probe with said target.

20. A method according to claim 19 further comprising:

adjusting said reference origin by both said first and second average values; and conducting said eddy current inspection of said target by said machine following said adjustment.

* * * * *